United States Patent [19]

Messina et al.

[11] Patent Number: 4,769,497

[45] Date of Patent: Sep. 6, 1988

[54] PROCESS FOR THE SYNTHESIS OF 2,2-DIALKOXY-PROPANES

[75] Inventors: Giuseppe Messina, Alghero-Sassari; Mario D. Moretti, Sassari; Gavino Sanna, Osilo-Sassari; Salvatore R. Sanna, Sorso-Sassari; Giovanni Soma, Sassari, all of Italy

[73] Assignee: Enichem Anic S.p.A., Milan, Italy

[21] Appl. No.: 65,822

[22] Filed: Jun. 23, 1987

[30] Foreign Application Priority Data

Jul. 4, 1986 [IT] Italy ................................ 21033 A/86
Dec. 18, 1986 [IT] Italy ................................ 22747 A/86

[51] Int. Cl.$^4$ ...................... C07C 41/48; C07C 41/50
[52] U.S. Cl. ................................. 568/594; 568/605; 568/3; 549/448
[58] Field of Search ................................. 568/594, 605

[56] References Cited

U.S. PATENT DOCUMENTS 2,340,907  2/1941  Sussman et al. ................... 568/594

Primary Examiner—Howard T. Mars
Attorney, Agent, or Firm—Hedman, Gibson, Costigan & Hoare

[57] ABSTRACT

A new method of synthesis of a 2,2-dialkoxy-propane e.g. 2,2-dimethoxy-propane, is described through reaction of a cyclic ketal, e.g. 2,2-dimethyl-(1,3)-dioxolane, with a boric acid alkyl ester, e.g. boric acid trimethyl ester, in the presence of an acidic catalyst. The reaction may be carried out either in liquid or in vapor phase. In the latter case, heating of the thus obtained intermediate mixture to the reflux temperature should follow the catalytic step.

20 Claims, No Drawings

PROCESS FOR THE SYNTHESIS OF 2,2-DIALKOXY-PROPANES

The present invention relates to a new process for the synthesis of a 2,2-dialkoxy-propane, starting from a 2,2-dimethyl-(1,3)-dioxolane, through reaction of this last compound with a suitably selected boric acid alkyl ester in the presence of an acidic catalyst. More particularly, the present invention refers to a method of synthesis of a 2,2-dialkoxy-propane of general formula (I)

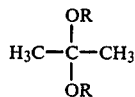
(I)

wherein
R represents a straight ($C_1$–$C_6$)alkyl radical, i.e. methyl, ethyl, propyl, n-butyl, n-pentyl, and n-hexyl,
starting from a 2,2-dimethyl-(1,3)-dioxolane of formula (II)

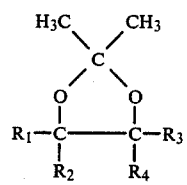
(II)

wherein
$R_1$, $R_2$, $R_3$, and $R_4$, each independently, may represent a hydrogen atom, an alkyl, cycloalkyl, aralkyl, or aryl radical,
through acid-catalysed reaction of this last compound with a suitably selected boric acid alkyl ester of formula (III)

(III)

wherein R is as defined above.

It is well known that acetals and ketals can be prepared through reaction of the corresponding aldehydes or ketones with alcohols in the presence of acidic catalysts (see J. Org. Chem. (1959), p.1731). However, as far as ketones, such as acetone, 2-methyl-butanone, methyl ethyl ketone, etc., are concerned, ketone acetals preparation by this method is rather difficult because ketal formation is an equilibrium reaction wherein the equilibrium lies far to the left: as an example, in the reaction of acetone with methanol, ketal equilibrium concentration, at 24° C., is only 11% by mole (see J. Org. Chem. (1959), p.1731) and, in order to get higher conversion percentages, it is necessary to carry out the reaction at lower temperatures (32% conversion, by mole, is obtained working at −28° C.).

Furthermore, in acetone ketalization with methanol, the reaction mixture consisting of acetone, methanol, $H_2O$ and 2,2-di-methoxy-propane can hardly be separated into its components because of the formation of binary and ternary azeotropes composed of acetone, methanol and di-methoxy-propane. Several different attempts have been made to overcome said problems: DE-OS No. 2,636,278, for instance, teaches that it is possible to drive the equilibrium toward the desired product side by conducting the reaction in the presence of calcium sulphate that adsorbs the reaction water; the hydrated calcium sulphate which forms must however be regenerated. DE-OS No. 2,929,827, on the other hand, teaches that by using excess acetone so as to afford the almost complete conversion of methanol, the problems involved in the separation of the reaction mixture, which are caused by the azeotrope formation, are greatly simplified. Finally, DE-OS No. 3,301,719 claims an indirect synthesis of 2,2-dimethoxypropane via trans-acetalization of 2,2-dimethyl-dioxolanes with methanol. This last method has the disadvantage that the methanol/2,2-dimethoxypropane azeotrope has to be solved in order to recover the desired product.

All these methods involve the use of an alkanol as reaction partner.

It has now been found and represents the first object of the present invention that it is possible to get a 2,2-dialkoxy-propane of formula (I) wherein R is as defined above, through reaction of a 2,2-dimethyl-(1,3)-dioxolane of formula (II), wherein $R_1$, $R_2$, $R_3$, and $R_4$, are as defined above, with a suitably selected boric acid ester of formula (III), wherein R is as defined above.

More particularly the reaction of the 2,2-dimethyl(1,3)-dioxolane (II) with the boric acid ester (III) can be carried out either in liquid or in vapour phase.

In the former case, the acid-catalysed reaction, which is simply carried out by contacting the two reaction partners in the presence of a homogeneous or heterogeneous acidic catalyst, directly affords the desired dialkoxy-propane, while in the latter case passing a mixture of the reactants, in vapour phase, over the heterogeneous catalyst must be followed by heating of the resulting intermediate mixture to the reflux temperature.

When the process of the invention is carried out in liquid phase, acidic catalysts which may suitably be employed are protic organic or inorganic acids, cation exchangers, metal halide type Lewis acid catalysts, mixtures of said metal halides with protic acids, and cupric salts. More particularly, suitable organic acids are, for instance, alkyl- and aryl-sulphonic acids e.g. methanesulphonic acid, trifluoromethanesulphonic acid, and p-toluenesulphonic acid, optionally halogenated aliphatic carboxylic acids, e.g. formic acid, acetic acid, propionic acid, fluoro- or chloro-acetic acids, trifluoro- or trichloro-acetic acids, trimethylacetic acid, citric acid, oxalic acid, and the like, aromatic carboxylic acids, e.g. benzoic acid, nitro- and halo-substituted benzoic acids, phenylacetic acid and the like. Suitable protic inorganic acids are, for instance, hydrochloric acid, hydrobromic acid, hydriodic acid, phosphoric acid, and sulfuric acid. Different types of cation exchangers with sulphonic, carboxylic, phosphoric or phenolic groupings attached to inert polymer supports such as styrene or styrene-divinylbenzene cross-linked polymers may suitably be employed.

The term "metal halide type Lewis acid catalysts", as used herein, designates Group IIb, IIIa, IVb, and Va halides such as, for instance, aluminum, antimony, arsenic, boron, phosphorous, mercury, zinc, zirconium, titanium, and the like metal halides, iron, silicon, and tin halides.

Examples of such metal halide type Lewis acids include $AlCl_3$, $ZnCl_2$, $SbF_5$, $SbCl_5$, $BF_3$, $FeCl_3$, $SiCl_4$, $SnCl_4$, etc.

Suitable cupric salts are, for instance, cupric halides, anhydrous cupric sulphate, cupric nitrate, cupric methansulphonates and, preferably, cupric trifluoromethanesulphonate.

Said acidic catalyst is typically employed in amounts ranging from 0.0001 and 1%, by weight, of the starting dioxolane, and preferably, ranging from 0.001 and 0.5%, depending on the particular type of acidic catalyst actually employed.

The reaction may be carried out, in liquid phase, by contacting either stoichiometric amounts of the reactants or an excess of either one so that dioxolane/trialkyl borate molar ratios comprised between 0.1 and 10, preferably between 0.2 and 2, and most preferably, between 0.2 and 0.5, can be used.

When carried out in liquid phase, the process of the invention is generally carried out at a temperature comprised between 0° C. and 200° C., and preferably, between room temperature and the reflux temperature of the reaction mixture.

Pressure is not critical; therefore, while the reaction is preferably carried out at atmospheric pressure, higher or lower pressures may also be applied, if desired.

At the end of the reaction, which is generally complete in a few hours and whose course can be easily monitored by chromatography, the desired 2,2-dialkoxy-propane is separated from the reaction mixture by conventional work-up procedures. In particular, the mixture is neutralized by the addition of a base, such as an alkali metal or alkaline-earth metal hydroxide or, preferably, an anion exchange resin, and the desired product is then recovered by fractional distillation. Said process may be carried out either as a batch or a continuous process. In a batch process, the starting dioxolane and boric acid trialkyl ester, in the suitably selected proportions, are made to react in the presence of a homogeneous or heterogeneous acidic catalyst, until the equilibrium is reached. The reaction mixture is then neutralized and distilled to separate the unreacted trialkyl borate first, and the desired 2,2-dialkoxy-propane then. The hold-up product which comprises unreacted dioxolane, and glycol borates of formulas (IV), (V), and (VI)

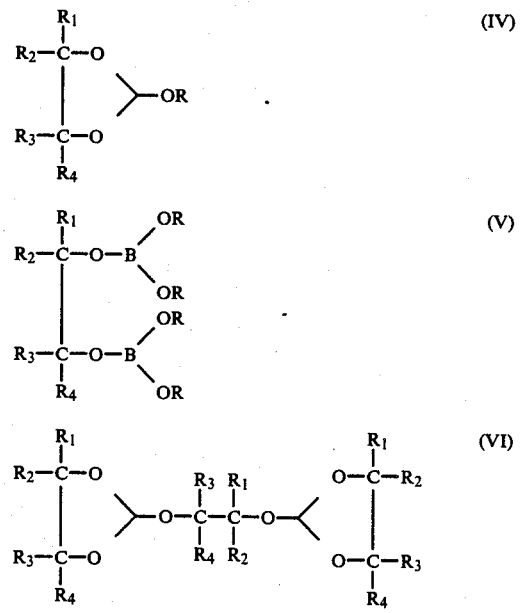

wherein R, $R_1$, $R_2$, $R_3$, and $R_4$ are as defined above, may be recycled to a new batch with fresh trialkyl borate or it can be charged to a distillation column together with a suitable amount of the alcohol ROH. Under these conditions the trialkyl borate (III) restores, according to the following equation

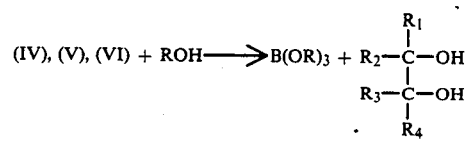

and is recovered by distillation.

In the continuous process, the reactants and the suitably selected acidic catalyst are fed to a reactor, or alternatively the reactants are fed to a reaction vessel containing the catalyst, the effluent is neutralized and the products are then separated from the unreacted starting compounds which are recycled. Recovery of the desired 2,2-dialkoxy-propane from the product mixture is then carried out as described for the batch process.

When carrying out the reaction in vapour phase, a mixture of the two reactants of formulas (II) and (III) is passed over a heterogeneous acidic catalyst, and the effluent is collected and heated to the reflux temperature, thus yielding the desired 2,2-dialkoxypropane.

The heterogeneous catalyst which is conveniently employed in the vapour phase process, is any of the so-called solid acidic oxides generally named as chalcides. These comprise silica, alumina, and the mixtures of alumina and silica, either natural or synthetic, in which other oxides such as chromia, magnesia, boria, molybdena, thoria, zirconia, and the like oxides, may also be present, as well as molybdenum sulfides (see to this purpose Friedel-Craft Chemistry - Wiley-Interscience Publisher (1973), pp.343-55).

Among the above mentioned oxides, alumina in its various forms and the diatomaceous earths generally used as catalysis supports or chromatography fillers, such as dicalite, celite, and chromosorb, proved to be particularly useful as the acidic catalyst. Good results are in fact obtained by using these products, previously acitvated at high temperatures (200°-1300° C.), as the reaction catalysts.

Also good results are obtained by using catalytic compositions obtained by coating one of the above mentioned oxides or oxide mixtures with boric acid, followed by its activation at a temperature comprised between 200° and 600° C.

The vapour phase process is preferably carried out by using a molar ratio (II)/(III) comprised between 10 and 0.5 and preferably between 5 and 1.

Suitable temperature and pressure values for this first step are those which allow contacting of the reactants with the catalyst in vapour phase.

In general, temperatures comprised between 100° and 400° C. proved to be useful to this purpose, even if a preferred temperature range is comprised between 180° and 280° C., and a most preferred temperature range is comprised between 200° and 250° C. It has been found in fact that the reaction rate at lower temperatures (100°-180° C.) is much lower, while at higher temperatures (>280° C.) also the rate of some undesired side-reactions increases.

This first step is conveniently carried out under atmospheric pressure. However higher or lower pressure values might as well be applied, provided the reaction temperature is such that passing of the reactants over the catalyst occurs in vapour phase. A contact time comprised between 10 and 600 seconds is applied in this first step to get satisfactory results, and typically a contact time comprised between 120 and 240 seconds is applied. Generally, the lower the temperature of this first step, the longer is the contact time needed. As an example, by operating at 200° C. and with an equimolar amount of the reactants, it is possible to get almost complete conversion of the reactants into a mixture of the desired intermediate compounds, with a contact time of 2-4 minutes, while with a contact time of 1 minute, a 40% conversion is achieved.

The reaction may also be carried out by feding, in addition to the reactants in vapour phase, also a carrier, selected from inert low-boiling compounds such as aliphatic hydrocarbons e.g. pentane, hexane, cyclohexane, and the like.

At the end of this first step, the effluent is collected and the thus obtained mixture is heated to the reflux temperature.

The mixture obtained from the first step contains equimolar amounts of an alkyl vinyl ether of formula (VII)

wherein R is as defined above, and of an alcohol ROH, unreacted alkyl borate and/or its reaction by-products, and small amounts of other minor products, besides any possibly unreacted 2,2-dimethyl-(1,3)-dioxolane.

It has been found that by heating said mixture to the reflux temperature, it is possible to get the addition of the alcohol to the alkyl vinyl ether yielding the desired 2,2-dialkoxy-propane.

The course of this latter step can be easily monitored by means of conventional chromatographic techniques. In particular, it has been observed that the reaction is substantially complete in a period of time generally comprised between 0.5 and 3 hours.

When the addition of the alcohol to the alkyl vinyl ether is complete, the desired product can be easily separated by distillation.

The addition in fact does proceed up to a substantially complete disappearance of the alcohol and therefore the problems of the prior-art methods concerning recovery of the product by azeotropic distillation of the methanol/dimethoxypropane azeotrope followed by recovery of dimethoxypropane from the azeotropic mixture, have been overcome.

A further object of the present invention is therefore a method of synthesis of a 2,2-dialkoxypropane of formula (I) by refluxing a mixture of an alkyl vinyl ether (VII) and an alcohol ROH, in substantially equimolar proportions, in the presence of a boric acid ester as the catalyst. The starting alkyl vinyl ethers may in fact be prepared also by other known methods such as for instance through alkoxylation of acetylenes.

In this case, it is not strictly required that the boric acid ester employed as the reaction catalyst in the addition of the alcohol ROH to the alkyl vinyl ether (VII), does contain the group ⌐|—OR but other boric acid esters can be employed as well, such as for instance other trialkyl or triaryl esters or cyclic esters, named 2-alkoxy-1,3,2-dioxaborolanes, of general formula (VIII)

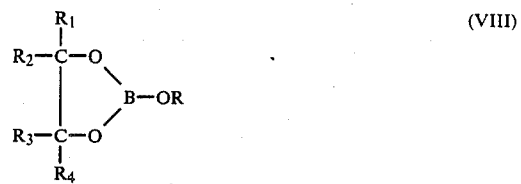

wherein $R_1$, $R_2$, $R_3$, and $R_4$ are as defined above. These last compounds can be prepared by known methods or by the first step described above.

The amount of boric acid ester employed in this second step is not critical. Generally however optimum results have been obtained using a % by weight of the ester, calculated on the mixture of the reaction partners, lower than 2.

The dioxolanes of formula (II) employed as starting materials in the process of the present invention can be easily synthesized by known literature methods, for instance, by reaction of aldehydes or ketones with oxiranes or glycols in the presence of acidic catalysts; also the boric esters (III) can be easily prepared starting from boric acid or boric anhydride and the alcohol ROH or through trans-esterification of conventional boric esters with the suitably selected alcohol ROH.

The following examples, which are aimed at better illustrating some representative embodiments of the process of the present invention, should in no way be interpreted as a limitation to the scopes of the invention itself.

EXAMPLES 1 TO 4

Examples of invention process carried out in liquid phase

Example 1

Boric acid trimethyl ester (448.1 g), 2,2-dimethyl-(1,3)-dioxolane (251.9 g) and 96% sulfuric acid (0.35 g) are charged into a three-necked 1000-ml flask equipped with a thermometer, a reflux condenser and a mechanical stirrer. The reaction mixture is refluxed (74.5° C.) under vigorous stirring for three hours. The obtained mixture contains 58.8 g (25% of the theory) of 2,2-dimethoxy-propane.

Example 2

Boric acid tri-methyl ester (587.1 g), 2,2-dimethyl(1,3)-dioxolane (112.9 g) and 96% $H_2SO_4$ (0.35 g) are mixed into a three-necked 1000-ml flask equipped as in example 1, and the reaction mixture is refluxed (71.3° C.) under vigorous stirring for three hours. The obtained mixture contains 2,2-dimethoxy-propane (56.7 g, 49.2% of the theory).

Example 3

Boric acid trimethyl ester (671.0 g), $Cu(CF_3SO_3)_2$ (0.4 g) and 2,2-dimethyl-(1,3)-dioxolane (129 g) are mixed together in a three-necked 1000-ml flask. The reaction mixture is heated to the reflux temperature (70.3° C.) under vigorous stirring for three hours yielding a mixture containing 2,2-dimethoxy-propane (66.2 g, 50.31%).

Example 4

Boric acid trimethyl ester (726 g), 96% H₂SO₄ (0.4 g) and 2,2-dimethyl-(1,3)-dioxolane (74 g) are mixed together in a three-necked 1000-ml flask. The reaction mixture is refluxed, under vigorous stirring, for one hour, then it is neutralized by the addition of NaOH and distilled in a fractional distillation adiabatic column, 1 m high and 1 inch in internal diameter, packed with Fenske rings.

Three fractions are separated: the first fraction to be distilled off consists of unreacted boric acid trimethyl ester, the second one consists of the desired 2,2-dimethoxy-propane (43.8 g, 58%), and the third one consists of unreacted 2,2-dimethyl-(1,3)-dioxolane. The hold-up in the column consists of boric acid glycol esters which are then trans-esterified with methanol to give boric acid trimethyl ester in quantitative yields (this last compound is distilled as the borate/methanol azeotrope) and ethylene glycol which is left in the column.

Examples 5 to 7

Examples of invention process carried out in vapour phase

Example 5

(a) Preparation of the catalytic bed

Al₂O₃ pellets (100 ml, 73 g) 2÷5 mm in diameter, are activated at 400° C. for 4 hours and then poured into a jacketed cylindrical reaction vessel (φi=1"; h=25 cm). The reaction vessel is heated to 200° C. and boric acid trimethyl ester heated to the same temperature is continuously flowed from the top to the bottom of the reaction vessel at 50 g/h. The effluent which is collected contains, besides boric acid trimethyl ester, relevant amounts of methanol which forms by reaction of trimethyl borate with the alumina hydroxy groups. Methanol formation and the concomitant absorption of boron by the catalyst ceases after 2 hours.

(b) First step

A mixture consisting of:

| | |
|---|---|
| boric acid trimethyl ester | 49.67% w. |
| 2,2-dimethyl-(1,3)-dioxolane | 50.33% w. | is fed, under the same reaction conditions as above, at 35 g/h, to the reaction vessel, yielding an effluent having the following composition:

| | |
|---|---|
| dimethylether | 0.28% w. |
| methanol | 6.81% w. |
| acetone | 0.35% w. |
| 2-methoxy-propene | 15.61% w. |
| boric acid trimethyl ester | 26.10% w. |
| 2,2-dimethoxy-propane | 0.60% w. |
| 2,2-dimethyl-(1,3)-dioxolane | 27.19% w. |
| 2-methoxy-1,3,2-dioxaborolane | 23.06% w. | corresponding to a 46.32% conversion of the starting 2,2-dimethyl-(1,3)-dioxolane and a 94.84% selectivity in 2-methoxy-propene.

(c) Second step

The effluent recovered in the foregoing step, having the composition indicated above, is seated to the reflux temperature for about 2 hours. A mixture is obtained having the following composition:

| | |
|---|---|
| dimethylether | 0.28% w. |
| methanol | |
| acetone | 0.35% w. |
| 2-methoxy-propene | 0.28% w. |
| boric acid trimethyl ester | 26.10% w. |
| 2,2-dimethoxy-propane | 22.74% w. |
| 2,2-dimethyl-(1,3)-dioxolane | 27.19% w. |
| 2-methoxy-1,3,2-dioxaborolane | 23.06% w. | corresponding to an almost complete conversion of the starting 2-methoxy-propene and methanol in 2,2-dimethoxy-propane.

More particularly, % conversions of 2-methoxy-propene and methanol are 100 and 98.5% respectively and selectivity in 2,2-dimethoxy-propane is 100%.

Example 6

(a) First step

A diatomaceous earth (100 ml, 37 g), calcined and crushed in particles of 30–60 mesh, is charged into a jacketed reaction vessel (φi=1"; h=25 cm). The reaction vessel is heated to 250° C. and a mixture consisting of:

| | |
|---|---|
| boric acid trimethyl ester | 33.51% w. |
| 2,2-dimethyl-(1,3)-dioxolane | 66.49% w. | vaporized at the same reaction temperature as above, is flowed, at 35 g/h, from the top of the reaction vessel. The effluent which is collected has the following composition:

| | |
|---|---|
| dimethylether | 0.12% w. |
| methanol | 9.14% w. |
| acetone | 0.15% w. |
| 2-methoxy-propene | 20.56% w. |
| boric acid trimethyl ester | 3.27% w. |
| 2,2-dimethoxy-propane | 0.34% w. |
| 2,2-dimethyl-(1,3)-dioxolane | 36.77% w. |
| 2-methoxy-1,3,2-dioxaborolane | 29.65% w. | which corresponds to a 44.7% conversion of the starting 2,2-dimethyl-(1,3)-dioxolane and a 98% selectivity in 2-methoxy-propene.

(b) Second step

The effluent recovered in the foregoing step, having the above reported composition, is heated to the reflux temperature for about 60 minutes. A mixture is obtained having the following composition:

| | |
|---|---|
| dimethylether | 0.12% w. |
| acetone | 0.15% w. |
| boric acid trimethyl ester | 3.27% w. |
| 2,2-dimethoxy-propane | 30.02% w. |
| 2,2-dimethyl-(1,3)-dioxolane | 36.77% w. |
| 2-methoxy-1,3,2-dioxaborolane | 29.67% w. | corresponding to a quantitative conversion of the starting 2-methoxy-propene and methanol in 2,2-dimethoxy-propane.

Example 7

(a) First step

A mixture consisting of:

| | |
|---|---|
| boric acid trimethyl ester | 50.47% w. |

| | |
|---|---|
| -continued | |
| 2,2-dimethyl-(1,3)-dioxolane | 49.53% w. | is fed, at 20 g/h, to the above reaction vessel, under the same reaction conditions as above. The effluent which is collected has the following composition:

| | |
|---|---|
| dimethylether | 0.17% w. |
| methanol | 10.93% w. |
| acetone | 0.21% w. |
| 2-methoxy-propene | 24.61% w. |
| boric acid trimethyl ester | 14.34% w. |
| 2,2-dimethoxy-propane | 0.29% w. |
| 2,2-dimethyl-(1,3)-dioxolane | 14.01% w. |
| 2-methoxy-1,3,2-dioxaborolane | 35.44% w. | corresponding to a 71.7% conversion of the starting 2,2-dimethyl-(1,3)-dioxolane and a 98.1% selectivity in 2-methoxy-propene.

(b) Second step

The effluent recovered in the foregoing step, having the above reported composition, is heated to the reflux temperature for about 30 minutes. A mixture is obtained having the following composition:

| | |
|---|---|
| dimethylether | 0.17% w. |
| acetone | 0.21% w. |
| boric acid trimethyl ester | 14.34% w. |
| 2,2-dimethoxy-propane | 35.83% w. |
| 2,2-dimethyl-(1,3)-dioxolane | 14.01% w. |
| 2-methoxy-1,3,2-dioxaborolane | 35.44% w. | corresponding to a quantitative conversion of the starting 2-methoxy-propene and methanol in 2,2-dimethoxy-propane.

We claim:

1. A process for preparing a 2,2-dialkoxy-propane of general formula (I)

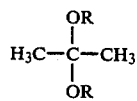

wherein R represents a straight ($C_1$-$C_6$)alkyl radical, which comprises contacting a 2,2-dimethyl-(1,3)-dioxolane of formula (II)

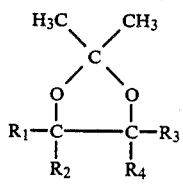

wherein $R_1$, $R_2$, $R_3$, and $R_4$, each independently, represent a hydrogen atom, an alkyl, cycloalkyl, aralkyl, or aryl radical, with a suitably selected boric acid alkyl ester of formula (III)

B(OR)$_3$ (III)

wherein R is as defined above, in the presence of an acidic catalyst.

2. The process of claim 1 wherein the reaction is carried out in liquid phase.

3. The process of claim 2 wherein the acidic catalyst which is employed in amounts comprised between 0.0001 and 1%, by weight, of the starting dioxolane, is selected from the group consisting of organic and inorganic protic acids, cation exchangers, Group IIb, IIIa, IVb, and Va halides, iron, tin or silicon halides, mixtures of said halides with protic acids, and cupric salts.

4. The process of claim 2 wherein the reaction is carried out at a temperature comprised between 0° and 200° C.

5. The process of claim 4 wherein the temperature is comprised between room temperature and the reflux temperature of the reaction mixture.

6. The process of claim 2 wherein the molar ratio between dioxolane (II) and trialkyl borate (III) is comprised between 0.1 and 10.

7. The process of claim 6 wherein said molar ratio is comprised between 0.2 and 2.

8. The process of claim 1 wherein contacting of the reactants in the presence of the acidic catalyst is carried out in vapour phase and is followed by heating of the thus obtained intermediate mixture to the reflux temperature.

9. The process of claim 8 wherein the acidic catalyst is selected from the solid acidic oxides, generally termed as chalcides.

10. The process of claim 9 wherein said catalyst is selected from silica, alumina, and the mixtures of silica and alumina, either natural or synthetic, in which other oxides such as chromia, magnesia, boria, molybdena, thoria, zirconia as well as molybdenum sulfide may be also present.

11. The process of claim 8 wherein 2,2-dimethyl-(1,3)-dioxolane (II) and boric acid trialkyl ester (III) are employed in a molar ratio (II)/(III) comprised between 10 and 0.5.

12. The process of claim 11 wherein said molar ratio is comprised between 5 and 1.

13. The process of claim 8 wherein the mixture of 2,2-dimethyl-(1,3)-dioxolane of formula (II) and boric acid trialkyl ester of formula (III) is passed over the catalyst bed at a temperature comprised between 100° and 400° C.

14. The process of claim 13 wherein said temperature is comprised between 180° and 280° C.

15. The process of claim 8 wherein the contact time of the mixture of 2,2-dimethyl-(1,3)-dioxolane of formula (II) and boric acid ester of formula (III) with the catalyst is comprised between 10 and 600 seconds.

16. The process of claim 1 for preparing a 2,2-dialkoxy-propane of formula (I) wherein R is methyl.

17. The process of claim 1 wherein 2,2-dimethyl-(1,3)-dioxolane is employed as the starting compound of formula (II).

18. A process for the synthesis of a 2,2-dialkoxy-propane of formula (I)

wherein R represents a straight ($C_1$-$C_6$)alkyl radical, which comprises heating to the reflux temperature a substantially equimolar mixture of an alkyl vinyl ether (VII)

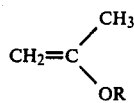  (VII)

wherein R is as defined above, and of an alcohol ROH wherein R is as defined above, in the presence of a boric acid ester as the catalyst.

19. The process of claim 18 wherein the boric acid ester employed as the reaction catalyst is selected from trialkyl esters, triaryl esters and cyclic esters of formula (VIII)

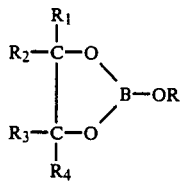  (VIII)

wherein R, $R_1$, $R_2$, $R_3$, and $R_4$, each independently, represent a hydrogen atom, an alkyl, cycloalkyl, aralkyl or aryl radical, and R is as defined above.

20. The process of claim 19 wherein the boric acid ester is a trialkyl ester of formula (III)

$$B(OR)_3 \qquad (III)$$

wherein R is as defined above.

* * * * *